US006258568B1

(12) United States Patent
Nyren

(10) Patent No.: US 6,258,568 B1
(45) Date of Patent: Jul. 10, 2001

(54) METHOD OF SEQUENCING DNA BASED ON THE DETECTION OF THE RELEASE OF PYROPHOSPHATE AND ENZYMATIC NUCLEOTIDE DEGRADATION

(75) Inventor: Pal Nyren, Skarpnack (SE)

(73) Assignee: Pyrosequencing AB, Uppsala (SE)

(*) Notice: Subject to any disclaimer, the term of this patent is extended or adjusted under 35 U.S.C. 154(b) by 0 days.

(21) Appl. No.: 09/331,517

(22) PCT Filed: Dec. 22, 1997

(86) PCT No.: PCT/GB97/03518
§ 371 Date: Jul. 23, 1999
§ 102(e) Date: Jul. 23, 1999

(87) PCT Pub. No.: WO98/28440
PCT Pub. Date: Jul. 2, 1998

(30) Foreign Application Priority Data

Dec. 23, 1996 (GB) .................................................. 9626815

(51) Int. Cl.[7] ...................................................... C12P 19/34
(52) U.S. Cl. ........................................ 435/91.1; 435/91.2
(58) Field of Search ................................ 435/91.1, 91.2, 435/810

(56) References Cited

U.S. PATENT DOCUMENTS

| 4,851,331 | 7/1989 | Vary et al. ................................ 435/6 |
| 4,863,849 | 9/1989 | Melamede ................................ 435/6 |
| 4,971,903 | 11/1990 | Hyman ..................................... 435/6 |
| 5,302,509 | 4/1994 | Cheesemann ........................... 435/6 |
| 5,405,746 | 4/1995 | Uhlen ..................................... 435/6 |
| 5,498,523 | 3/1996 | Tabor et al. ............................. 435/6 |
| 5,534,407 | 7/1996 | Tabor et al. ............................. 435/5 |
| 5,534,424 | 7/1996 | Uhlen et al. ........................ 435/91.2 |

(List continued on next page.)

FOREIGN PATENT DOCUMENTS

| 3546374 | 7/1987 | (DE) . |
| 414178 | 6/1993 | (DE) . |
| 19602662 | 8/1997 | (DE) . |

(List continued on next page.)

OTHER PUBLICATIONS

Sanger et al., "DNA sequencing with chain–terminating inhibitors", *Proc. Natl. Acad. Sci USA*, 1977, vol. 74, No. 12, pp. 5463–5467.
*STRATAGENE* Catalog 1988, 2 pages.
U.S. application No. 09/269436, Nyren et al., filed Jul. 6, 1999.
Fu et al. (1997) Nucleic Acids Research 25:677.
Jones (1997) Bio Techniques 22:938.
Zimmerman (1990) Nucleic Acids Research 18:1067.
Ronaghi et al., Science 281, 363 & 365 (1998).*
Benkovic et al. (1995) Methods in Enzymology 262:257.
Gupta et al. (1984) Nucleic Acids Research 12:5897.
Hultman et al. (1990) Nucleic Acids Research 18:5107.
Hyman (1988) Analytical Biochemistry 174:423.
Kajiyama et al. (1994) Biosci. Biotech. Biochem. 58:1170.
LeBel et al. (1980) J. Biol. Chem. 256:1227.
Nyren (1987) Analytical Biochemistry 167:235.
Nyren (1993) Analytical Biochemistry 208:171.
Nyren et al. (1985) Analytical Biochemistry 151:504.
Patel et al. (1991) Biochemistry 30:511.
Ronaghi et al. (1996) Analytical Biochemistry 242:84.
Syvanen et al. (1990) Genomics 8:684.
Vosberg et al. (1977) Biochemistry 16:3633.
Wong et al. (1991) Biochemistry 30:526.

*Primary Examiner*—Kenneth R. Horlick
(74) *Attorney, Agent, or Firm*—Baker Botts

(57) ABSTRACT

The present invention relates to a method of sequencing DNA, based on the detection of base incorporation by the release of pyrophosphate (PPi) and simultaneous enzymatic nucleotide degradation.

17 Claims, 6 Drawing Sheets

U.S. PATENT DOCUMENTS

| | | | |
|---|---|---|---|
| 5,599,675 | 2/1997 | Brenner et al. | 435/6 |
| 5,665,545 | 9/1997 | Malek et al. | 435/6 |
| 5,674,716 | 10/1997 | Tabor et al. | 435/91.1 |
| 5,679,524 | 10/1997 | Nikiforov et al. | 435/6 |
| 5,834,189 | 11/1998 | Stevens et al. | 435/6 |
| 5,849,487 | 12/1998 | Hase et al. | 435/6 |
| 5,856,092 | 1/1999 | Dale et al. | 435/6 |
| 5,888,819 | 3/1999 | Goelet et al. | 435/5 |

FOREIGN PATENT DOCUMENTS

| | | |
|---|---|---|
| 0054676 | 6/1982 | (EP). |
| 0223618 | 5/1987 | (EP). |
| 0298669 | 1/1989 | (EP). |
| 0412883 | 2/1991 | (EP). |
| 0566140 | 10/1993 | (EP). |
| 0663447 | 7/1995 | (EP). |
| 0701625 | 3/1996 | (EP). |
| 0756637 | 2/1997 | (EP). |
| 2674254 | 9/1992 | (FR). |
| WO 8909283 | 10/1989 | (WO). |
| WO 8912063 | 12/1989 | (WO). |
| 9004649 | 5/1990 | (WO). |
| 9105065 | 4/1991 | (WO). |
| WO 9106678 | 5/1991 | (WO). |
| WO 9113075 | 9/1991 | (WO). |
| 9206219 | 4/1992 | (WO). |
| 9216654 | 10/1992 | (WO). |
| WO 9321340 | 10/1993 | (WO). |
| 9323415 | 11/1993 | (WO). |
| WO 9323562 | 11/1993 | (WO). |
| WO 9323563 | 11/1993 | (WO). |
| WO 9323564 | 11/1993 | (WO). |
| WO 9417198 | 8/1994 | (WO). |
| 9610640 | 4/1996 | (WO). |
| 9629424 | 9/1996 | (WO). |
| 9855653 | 12/1998 | (WO). |
| 9905315 | 2/1999 | (WO). |
| 0011222 | 3/2000 | (WO). |

* cited by examiner

METHOD OF SEQUENCING DNA BASED ON THE DETECTION OF THE RELEASE OF PYROPHOSPHATE AND ENZYMATIC NUCLEOTIDE DEGRADATION

BACKGROUND OF THE INVENTION

This invention relates to a method of sequencing DNA, based on the detection of base incorporation by the release of pyrophosphate (PPi) and simultaneous enzymatic nucleotide degradation.

DNA sequencing is an essential tool in molecular genetic analysis. The ability to determine DNA nucleotide sequences has become increasingly important as efforts have commenced to determine the sequences of the large genomes of humans and other higher organisms. The two most commonly used methods for DNA sequencing are the enzymatic chain-termination method of Sanger and the chemical cleavage technique of Maxam and Gilbert. Both methods rely on gel electrophoresis to resolve, according to their size, DNA fragments produced from a larger DNA segment. Since the electrophoresis step as well as the subsequent detection of the separated DNA-fragments are cumbersome procedures, a great effort has been made to automate these steps. However, despite the fact that automated electrophoresis units are commercially available, electrophoresis is not well suited for large-scale genome projects or clinical sequencing where relatively costeffective units with high throughput are needed. Thus, the need for non-electrophoretic methods for sequencing is great and several alternative strategies have been described, such as scanning tunnel electron microscopy (Driscoll et al., 1990, Nature, 346, 294–296), sequencing by hybridization (Bains et al., 1988, J. Theo. Biol. 135, 308–307) and single molecule detection (Jeff et al., 1989, Biomol. Struct. Dynamics, 7, 301–306), to overcome the disadvantages of electrophoresis.

Techniques enabling the rapid detection of a single DNA base change are also important tools for genetic analysis. In many cases detection of a single base or a few bases would be a great help in genetic analysis since several genetic diseases and certain cancers are related to minor mutations. A mini-sequencing protocol based on a solid phase principle was described (Hultman, et al., 1988, Nucl. Acid. Res., 17, 4937–4946; Syvanen et al., 1990, Genomics, 8, 684–692). The incorporation of a radiolabeled nucleotide was measured and used for analysis of the three-allelic polymorphism of the human apolipoprotein E gene. However, radioactive methods are not well suited for routine clinical applications and hence the development of a simple non-radioactive method for rapid DNA sequence analysis has also been of interest.

Methods of sequencing based on the concept of detecting inorganic pyrophosphate (PPi) which is released during a polymerase reaction have been described (WO 93/23564 and WO 89/09283). As each nucleotide is added to a growing nucleic acid strand during a polymerase reaction, a pyrophosphate molecule is released. It has been found that pyrophosphate released under these conditions can be detected enzymically e.g. by the generation of light in the luciferase-luciferin reaction. Such methods enable a base to be identified in a target position and DNA to be sequenced simply and rapidly whilst avoiding the need for electrophoresis and the use of harmful radiolabels.

However, the PPi-based sequencing methods mentioned above are not without drawbacks. The template must be washed thoroughly between each nucleotide addition to remove all non-incorporated deoxynucleotides. This makes it difficult to sequence a template which is not bound to a solid support. In addition new enzymes must be added with each addition of deoxynucleotide.

Thus, whilst PPi-based methods such as are described above do represent an improvement in ease and speed of operation, there is still a need for improved methods of sequencing which allow rapid detection and provision of sequence information and which are simple and quick to perform, lending themselves readily to automation.

We now propose a novel modified PPi-based sequencing method in which these problems are addressed and which permits the sequencing reactions to be performed without intermediate washing steps, enabling the procedure to be carried out simply and rapidly, for example in a single microtitre plate. Advantageously, there is no need to immobilise the DNA. Conveniently, and as will be discussed in more detail below, the new method of the invention may also readily be adapted to permit the sequencing reactions to be continuously monitored in real-time, with a signal being generated and detected, as each nucleotide is incorporated.

BRIEF SUMMARY OF THE INVENTION

In one aspect, the present invention thus provides a method of identifying a base at a target position in a sample DNA sequence wherein an extension primer, which hybridises to the sample DNA immediately adjacent to the target position is provided and the sample DNA and extension primer are subjected to a polymerase reaction in the presence of a deoxynucleotide or dideoxynucleotide whereby the deoxynucleotide or dideoxynucleotide will only become incorporated and release pyrophosphate (PPi) if it is complementary to the base in the target position, any release of PPi being detected enzymically, different deoxynucleotides or dideoxynucleotides being added either to separate aliquots of sample-primer mixture or successively to the same sample-primer mixture and subjected to the polymerase reaction to indicate which deoxynucleotide or dideoxynucleotide is incorporated, characterised in that, a nucleotide-degrading enzyme is included during the polymerase reaction step, such that unincorporated nucleotides are degraded.

DETAILED DESCRIPTION OF THE INVENTION

Figure 1:
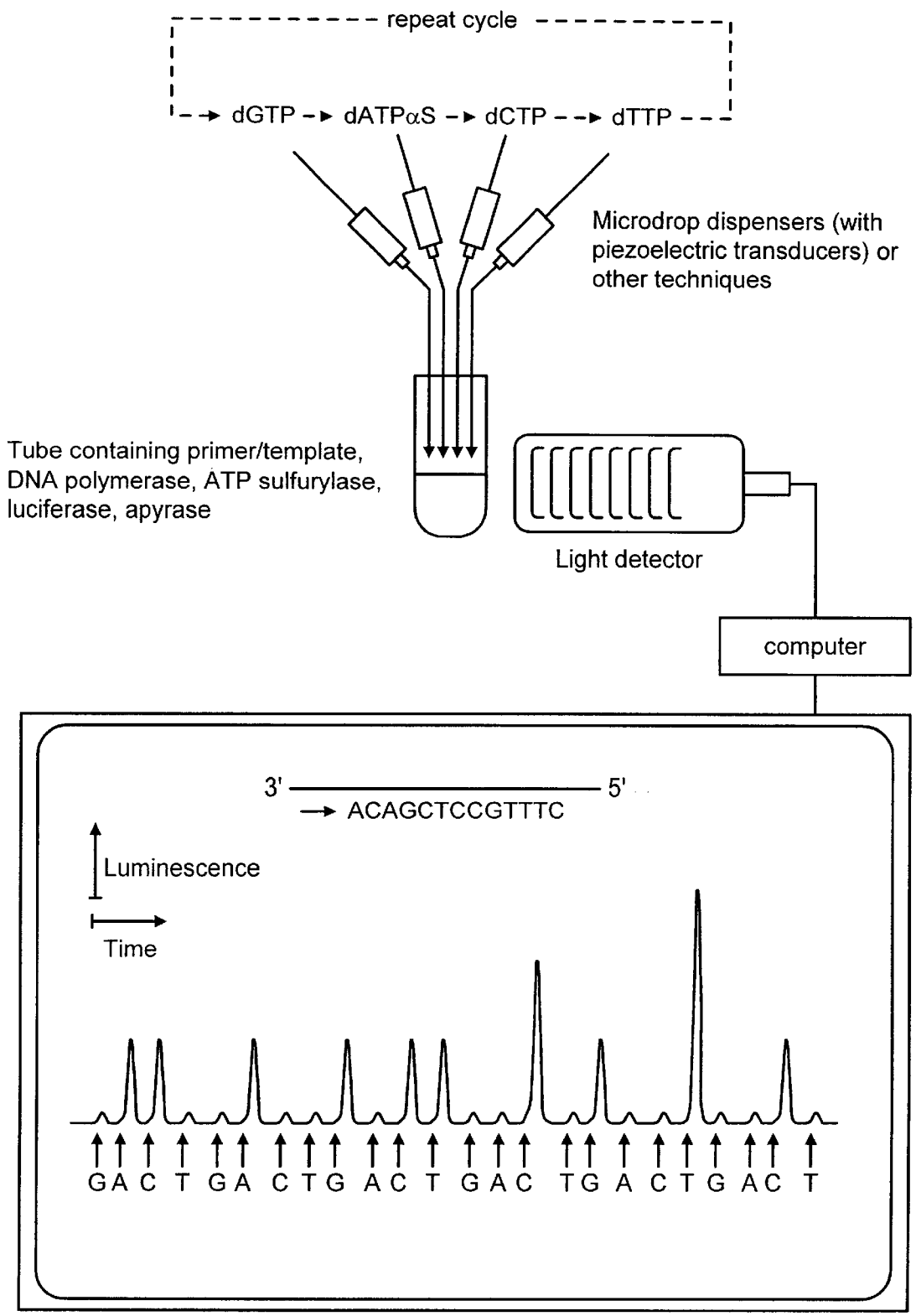
FIG. 1 is a schematic representation of a new DNA sequencing method of the invention. The four different nucleotides are added stepwise to the template hybridised to a primer. The PPi released in the DNA polymerase catalysed reaction, is detected by the ATP sulfurylase and luciferase catalysed reactions. The height of the signal is proportional to the number -of bases which have been incorporated. The added nucleotides are continuously degraded by a nucleotide degrading enzyme. After the first added nucleotide is degraded, the next nucleotide can be added. These steps are repeated in a cycle and the sequence of the template is deduced.

The term "nucleotide-degrading enzyme" as used herein includes all enzymes capable of non-specifically degrading nucleotides, including at least nucleoside triphosphates (NTPs), but optionally also di- and mono-phosphates, and any mixture or combination of such enzymes, provided that a nucleoside triphosphatase or other NTP degrading activity is present. Although nucleotide-degrading enzymes having a phosphatase activity may conveniently be used according to the invention, any enzyme having any nucleotide or nucleoside degrading activity may be used, e.g. enzymes which cleave nucleotides at positions other than at the phosphate group, for example at the base or sugar residues. Thus, a nucleoside triphosphate degrading enzyme is essential for the invention. Nucleoside di- and/or mono-phosphate degrading enzymes are optional and may be used in combination with a nucleoside tri-phosphate degrading enzyme. Suitable such enzymes include most notably apyrase which is both a nucleoside diphosphatase and triphosphatase, catalysing the reactions NTP→NMP+2Pi and NTP→NDP+Pi (where NTP is a nucleoside triphosphate, NDP is a nucleoside diphospate, NMP is a nucleotide monophosphate and Pi is phosphate). Apyrase may be obtained from Sigma Chemical Company. Other suitable nucleotide triphosphate degrading enzymes include Pig Pancreas nucleoside triphosphate diphosphohydrolase (Le Bel et al., 1980, J. Biol. Chem., 255, 1227–1233). Further enzymes are described in the literature.

Different combinations of nucleoside tri-, di- or monophosphatases may be used. Such enzymes are described in the literature and different enzymes may have different characteristics for deoxynucleotide degradation, eg. different Km, different efficiencies for a different nucleotides etc. Thus, different combinations of nucleotide degrading enzymes may be used, to increase the efficiency of the nucleotide degradation step in any given system. For example, in some cases, there may be a problem with contamination with kinases which may convert any nucleoside diphosphates remaining to nucleoside triphosphates, when a further nucleoside triphosphate is added. In such a case, it may be advantageous to include a nucleoside disphosphatase to degrade the nucleoside diphosphates. Advantageously all nucleotides may be degraded to nucleosides by the combined action of nucleoside tri-, di- and monophosphatases.

Generally speaking, the nucleotide-degrading enzyme is selected to have kinetic characteristics relative to the polymerase such that nucleotides are first efficiently incorporated by the polymerase, and then any non-incorporated nucleotides are degraded. Thus, for example, if desired the $k_m$ of the nucleotide-degrading enzyme may be higher than that of the polymerase such that nucleotides which are not incorporated by the polymerase are degraded. This allows the sequencing procedure to proceed without washing the template between successive nucleotide additions. A further advantage is that since washing steps are avoided, it is not necessary to add new enzymes eg. polymerase with each new nucleotide addition, thus improving the economy of the procedure. Thus, the nucleotide-degrading enzyme or enzymes are simply included in the polymerase reaction mix, and a sufficient time is allowed between each successive nucleotide addition for degradation of substantially most of the unincorporated nucleotides. The amount of nucleotide-degrading enzyme to be used, and the length of time between nucleotide additions may readily be determined for each particular system, depending on the reactants selected, reaction conditions etc. However, it has for example been found that the enzyme apyrase may conveniently be used in amounts of 0.25 U/mL to 2 U/mL.

As mentioned above, the nucleotide-degrading enzyme(s) may be included during the polymerase reaction step. This may be achieved simply by adding the enzyme(s) to the polymerase reaction mixture prior to, simultaneously with or after the polymerase reaction (ie. the chain extension or nucleotide incorporation) has taken place, e.g. prior to, simultaneously with, or after, the polymerase and/or nucleotides are added to the sample/primer.

In one embodiment, the nucleotide-degrading enzyme(s) may simply be included in solution in a reaction mix for the polymerase reaction, which may be initiated by addition of the polymerase or nucleotide(s).

Alternatively, the nucleotide-degrading enzyme(s) may be immobilised on a solid support e.g. a particulate solid support (e.g. magnetic beads) or a filter, or dipstick etc. and it may be added to the polymerase reaction mixture at a convenient time. For example such immobilised enzyme(s) may be added after nucleotide incorporation (i.e. chain extension) has taken place, and then, when the incorporated nucleotides are hydrolysed, the immobilised enzyme may be removed from the reaction mixture (e.g. it may be withdrawn or captured, e.g. magnetically in the case of magnetic beads), before the next nucleotide is added. The procedure may then be repeated to sequence more bases. Such an arrangement has the advantage that more efficient nucleotide degradation may be achieved as it permits more nucleotide degrading enzyme to be added for a shorter period. This arrangement may also facilitate optimisation of the balance between the two competing reactions of DNA polymerisation and nucleotide degradation.

In a further embodiment, the immobilisation of the nucleotide-degrading enzyme may be combined with the use of the enzyme(s) in solution. For example, a lower amount may be included in the polymerase reaction mixture and, when necessary, nucleotide-degrading activity may be boosted by adding immobilised enzyme as described above.

The term dideoxynucleotide as used herein includes all 2'-deoxynucleotides in which the 3'-hydroxyl group is absent or modified and thus, while able to be added to the primer in the presence of the polymerase, is unable to enter into a subsequent polymerisation reaction.

PPi can be determined by many different methods and a number of enzymatic methods have been described in the literature (Reeves et al., (1969), Anal. Biochem., 28, 282–287; Guillory et al., (1971), Anal. Biochem., 39, 170–180; Johnson et al., (1968), Anal. Biochem., 15, 273; Cook et al., (1978), Anal. Biochem. 91, 557–565; and Drake et al., (1979), Anal. Biochem. 94, 117–120).

It is preferred to use luciferase and luciferin in combination to identify the release of pyrophosphate since the amount of light generated is substantially proportional to the amount of pyrophosphate released which, in turn, is directly proportional to the amount of base incorporated. The amount of light can readily be estimated by a suitable light sensitive device such as a luminometer.

Luciferin-luciferase reactions to detect the release of PPi are well known in the art. In particular, a method for continuous monitoring of PPi release based on the enzymes ATP sulphurylase and luciferase has been developed by Nyrén and Lundin (Anal. Biochem., 151, 504–509, 1985) and termed ELIDA (Enzymatic Luminometric Inorganic Pyrophosphate Detection Assay). The use of the ELIDA method to detect PPi is preferred according to the present invention. The method may however be modified, for example by the use of a more thermostable luciferase (Kaliyama et al., 1994, Biosci. Biotech. Biochem., 58, 1170–1171) and/or ATP sulfurylase (Onda et al., 1996, Bioscience, Biotechnology and Biochemistry, 60:10, 1740–42). This method is based on the following reactions:

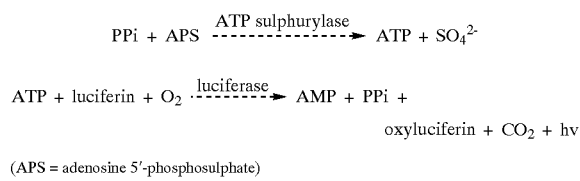

(APS = adenosine 5'-phosphosulphate)

The preferred detection enzymes involved in the PPi detection reaction are thus ATP sulphurylase and luciferase.

The method of the invention may be performed in two steps, as described for example in WO93/23564 and WO89/09283, firstly a polymerase reaction step ie. a primer extension step, wherein the nucleotide(s) are incorporated, followed by a second detection step, wherein the release of PPi is monitored or detected, to detect whether or not a nucleotide incorporation has taken place. Thus, after the polymerase reaction has taken place, samples from the polymerase reaction mix may be removed and analysed by the ELIDA eg. by adding an aliquot of the sample to a reaction mixture containing the ELIDA enzymes and reactants.

However, as mentioned above, the method of the invention may readily be modified to enable the sequencing (ie. base incorporation) reactions to be continuously monitored in real time. This may simply be achieved by performing the chain extension and detection, or signal-generation, reactions substantially simultaneously by including the "detection enzymes" in the chain extension reaction mixture. This represents a departure from the approach reported in the PPi-based sequencing procedures discussed in the literature above, in which the chain extension reaction is first performed separately as a first reaction step, followed by a separate "detection" reaction, in which the products of the extension reaction are subsequently subjected to the luciferin-luciferase based signal generation ("detection") reactions. This "real time" procedure represents a preferred embodiment of the invention.

To carry out this preferred embodiment of the method of the invention, the PPi-detection enzyme(s) are included in the polymerase reaction step ie. in the chain extension reaction step. Thus the detection enzymes are added to the reaction mix for the polymerase step prior to, simultaneously with or during the polymerase reaction. In the case of an ELIDA detection reaction, the reaction mix for the polymerase reaction may thus include at least nucleotide (deoxy- or dideoxy), polymerase, luciferin, APS, ATP suphurylase and luciferase together with a nucleotide-degrading enzyme. The polymerase reaction may be initiated by addition of the polymerase or, more preferably the nucleotide, and preferably the detection enzymes are already present at the time the reaction is initiated, or they may be added with the reagent that initiates the reaction.

This latter embodiment of the present invention thus permits PPi release to be detected during the polymerase reaction giving a real-time signal. The sequencing reactions may be continuously monitored in real-time. A procedure for rapid detection of PPi release is thus enabled by the present invention. The ELIDA reactions have been estimated to take place in less than 2 seconds (Nyrén and Lundin, supra). The rate limiting step is the conversion of PPi to ATP by ATP sulphurylase, while the luciferase reaction is fast and has been estimated to take less than 0.2 seconds. Incorporation rates for polymerases have also been estimated by various methods and it has been found, for example, that in the case of Klenow polymerase, complete incorporation of one base may take less than 0.5 seconds. Thus, the estimated total time for incorporation of one base and detection by ELIDA is approximately 3 seconds. It will be seen therefore that very fast reaction times are possible, enabling real-time detection. The reaction times could further be decreased by using a more thermostable luciferase. By using a nucleotide-degrading enzyme with a time in the order of seconds for degrading half the nucleotides present, an efficient degradation can be achieved in time frames from seconds to several minutes.

Thus, the method of the present invention may be performed in a single reaction step involving an up to 4-enzyme or more reaction mixture ie. a multi-enzyme mixture. It is surprising that a beneficial and cooperative effect between multiple interlinked enzyme reactions may take place according to the invention and yield beneficial results.

A coupled sequencing/detection system may therefore be based on the following reactions:

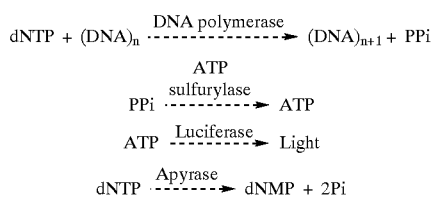

-continued

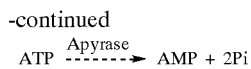

It will be noted that a nucleotide-degrading enzyme such as apyrase would also degrade the ATP not used in the luciferase reactions. Thus, all nucleotide triphosphates are degraded.

Indeed, when PPi release according to the invention is detected by luciferase-based reactions e.g. ELIDA, this ATP-degrading activity may be an important advantage, particularly in "turning off" the light production by the luciferin/luciferase reaction. This may also be of advantage, with a low "burn rate" of the luciferase enzyme.

A potential problem which has previously been observed with PPi-based sequencing methods is that DATP, used in the sequencing (chain extension) reaction, interferes in the subsequent luciferase-based detection reaction by acting as a substrate for the luciferase enzyme. This may be reduced or avoided by using, in place of deoxy- or dideoxy adenosine triphosphate (ATP), a DATP or ddATP analogue which is capable of acting as a substrate for a polymerase but incapable of acting as a substrate for a said PPi-detection enzyme.

The term "incapable of acting" includes also analogues which are poor substrates for the detection enzymes, or which are substantially incapable of acting as substrates, such that there is substantially no, negligible, or no significant interference in the PPi detection reaction.

Thus, a further preferred feature of the invention is the use of a dATP or ddATP analogue which does not interfere in the enzymatic PPi detection reaction but which nonetheless may be normally incorporated into a growing DNA chain by a polymerase and can also be degraded by the nucleotide degrading enzymes. By "normally incorporated" is meant that the nucleotide is incorporated with normal, proper base pairing. In the preferred embodiment of the invention where luciferase is the PPi detection enzyme, the preferred analogues for use according to the invention are the [1-thio] triphosphate (or α-thiotriphosphate) analogues of deoxy or dideoxy ATP, preferably deoxyadenosine [1-thio] triphospate, or deoxyadenosine α-thiotriphosphate (dATPαS) as it is also known. dATPαS, along with the α-thio analogues of dCTP, dGTP and dTTP, may be purchased from New England Nuclear Labs. Experiments have shown that substituting DATP with dATPαS allows efficient incorporation by the polymerase with a low background signal due to the absence of an interaction between dATPαS and luciferase. The signal-to-noise ratio is increased by using a nucleotide analogue in place of dATP, which eliminates the background caused by the ability of dATP to function as a substrate for luciferase. In particular, an efficient incorporation with the polymerase may be achieved while the background signal due to the generation of light by the luciferin-luciferase system resulting from dATP interference is substantially decreased. The dNTPαS analogues of the other nucleotides may also be used in place of all dNTPs.

The sample DNA (ie. DNA template) may conveniently be single-stranded, and may either by immobilised on a solid support or in solution. The use of a nucleotide-degrading enzyme according to the present invention means that it is not necessary to immobilise the template DNA to facilitate washing, since a washing step is no longer required. By using thermostable enzymes, double-stranded DNA templates might also be used.

The sample DNA may be provided by any desired source of DNA, including for example PCR or other amplified fragments, inserts in vectors such as M13 or plasmids.

In order to repeat the method cyclically and thereby sequence the sample DNA and, also to aid separation of a single stranded sample DNA from its complementary strand, the sample DNA may optionally be immobilised or provided with means for attachment to a solid support. Moreover, the amount of sample DNA available may be small and it may therefore be desirable to amplify the sample DNA before carrying out the method according to the invention.

The sample DNA may be amplified, and any method of amplification may be used, for example in vitro by PCR or Self Sustained Sequence Replication (3SR) or in vivo using a vector and, if desired, i vitro and in vivo amplification may be used in combination. Whichever method of amplification is used the procedure may be modified that the amplified DNA becomes immobilised or is provided with means for attachment to a solid support. For example, a PCR primer may be immobilised or be provided with means for attachment to a solid support. Also, a vector may comprise means for attachment to a solid support adjacent the site of insertion of the sample DNA such that the amplified sample DNA and the means for attachment may be excised together.

Immobilisation of the amplified DNA may take place as part of PCR amplification itself, as where one or more primers are attached to a support, or alternatively one or more of the PCR primers may carry a functional group permitting subsequent immobilisation, eg. a biotin or thiol group. Immobilisation by the 5' end of a primer allows the strand of DNA emanating from that primer to be attached to a solid support and have its 3' end remote from the support and available for subsequent hybridisation with the extension primer and chain extension by polymerase.

The solid support may conveniently take the form of microtitre wells, which are advantageously in the conventional 8×12 format, or dipsticks which may be made of polystyrene activated to bind the primer DNA (K Almer, Doctoral Theses, Royal Institute of Technology, Stockholm, Sweden, 1988). However, any solid support may conveniently be used including any of the vast number described in the art, eg. for separation/immobilisation reactions or solid phase assays. Thus, the support may also comprise particles, fibres or capillaries made, for example, of agarose, cellulose, alginate, Teflon or polystyrene. Magnetic particles eg the superparamagnetic beads produced by Dynal AS (Oslo, Norway) also may be used as a support.

The solid support may carry functional groups such as hydroxyl, carboxyl, aldehyde or amino groups, or other moieties such as avidin or streptavidin, for the attachment of primers. These may in general be provided by treating the support to provide a surface coating of a polymer carrying one of such functional groups, e.g. polyurethane together with a polyglycol to provide hydroxyl groups, or a cellulose derivative to provide hydroxyl groups, a polymer or copolymer of acrylic acid or methacrylic acid to provide carboxyl groups or an aminoalkylated polymer to provide amino groups. U.S. Pat. No. 4654267 describes the introduction of many such surface coatings.

Accumulation of reaction by-products may take place. This may readily be avoided by washing the sample after a certain number of reaction cycles e.g. 15–25. Washing may be facilitated by immobilising the sample on a solid surface.

The assay technique is very simple and rapid, thus making it easy to automate by using a robot apparatus where a large number of samples may be rapidly analysed. Since the preferred detection and quantification is based on a luminometric reaction, this can be easily followed spectrophotometrically. The use of luminometers is well known in the art and described in the literature.

The pyrophosphate detection method of the present invention thus opens up the possibility for an automated approach for large-scale, non-elecrophoretic sequencing procedures, which allow for continuous measurement of the progress of the polymerisation reaction with time. The method of the invention also has the advantage that multiple samples may be handled in parallel.

The target DNA may be cDNA synthesised from RNA in the sample and the method of the invention is thus applicable to diagnosis on the basis of characteristic RNA. Such preliminary synthesis can be carried out by a preliminary treatment with a reverse transcriptase, conveniently in the same system of buffers and bases of subsequent PCR steps if used. Since the PCR procedure requires heating to effect strand separation, the reverse transcriptase will be inactivated in the first PCR cycle. When mRNA is the sample nucleic acid, it may be advantageous to submit the initial sample, e.g. a serum sample, to treatment with an immobilised polydT oligonucleotide in order to retrieve all mRNA via the terminal polyA sequences thereof. Alternatively, a specific oligonucleotide sequence may be used to retrieve the RNA via a specific RNA sequence. The oligonucleotide can then serve as a primer for cDNA synthesis, as described in WO 89/0982.

Advantageously, the extension primer is sufficiently large to provide appropriate hybridisation with the sequence immediately 5' of the target position, yet still reasonably short in order to avoid unnecessary chemical synthesis. It will be clear to persons skilled in the art that the size of the extension primer and the stability of hybridisation will be dependent to some degree on the ratio of A-T to C-G base pairings, since more hydrogen bonding is available in a C-G pairing. Also, the skilled person will consider the degree of homology between the extension primer to other parts of the amplified sequence and choose the degree of stringency accordingly. Guidance for such routine experimentation can be found in the literature, for example, Molecular Cloning: a laboratory manual by Sambrook, J., Fritsch E. F. and Maniatis, T. (1989). It may be advantageous to ensure that the sequencing primer hybridises at least one base inside from the 3' end of the template to eliminate blunt-ended DNA polymerase activity. If separate aliquots are used (ie. 4 aliquots, one for each base), the extension primer is preferably added before the sample is divided into four aliquots although it may be added separately to each aliquot. It should be noted that the extension primer may be identical with the PCR primer but preferably it is different, to introduce a further element of specificity into the system.

Alternatively, a primer with a phosphorylated 5'-end, containing a loop and annealing back on itself and the 3'-end of the single stranded template can be used. If the 3'-end of the template has the sequence region denoted T (template), the primer has the following sequence starting from the 5'-end; P-L-P'-T', where P is primer specific (5 to 30 nucleotides), L is loop (preferably 4 to 10 nucleotides), P' is complementary to P (preferably 5 and 30 nucleotides) and T' is complementary to the template sequence in the 3'-end (T) (at least 4 nucleotides). This primer can then be ligated to the single stranded template using T4 DNA ligase or a similar enzyme. This provides a covalent link between the template and the primer, thus avoiding the possibility that the hybridised primer is washed away during the protocol.

The polymerase reaction in the presence of the extension primer and a deoxynucleotide is carried out using a polymerase which will incorporate dideoxynucleotides, e.g. T7 polymerase, Klenow or Sequenase Ver. 2.0 (USB U.S.A.). Any suitable polymerase may conveniently be used and many are known in the art and reported in the literature. However, it is known that many polymerases have a proof-reading or error checking ability and that 3' ends available for chain extension are sometimes digested by one or more nucleotides. If such digestion occurs in the method according to the invention the level of background noise increases. In order to avoid this problem, a nonproof-reading polymerase, eg. exonuclease deficient (exo$^-$) Klenow polymerase may be used. Otherwise it is desirable to add fluoride ions or nucleotide monophosphates which suppress 3' digestion by polymerase. The precise reaction conditions, concentrations of reactants etc. may readily be determined for each system according to choice. However, it may be advantageous to use an excess of polymerase over primer/template to ensure that all free 3' ends are extended.

In the method of the invention there is a need for a DNA polymerase with high efficiency in each extension step due to the rapid increase of background signal which may take place if templates which are not fully extended accumulate. A high fidelity in each step is also desired, which can be achieved by using polymerases with exonuclease activity. However, this has the disadvantage mentioned above that primer degradation can be obtained. Although the exonuclease activity of the Klenow polymerase is low, we have found that the 3' end of the primer was degraded with longer incubations in the absence of nucleotides. An induced-fit binding mechanism in the polymerisation step selects very efficiently for binding of the correct DNTP with a net contribution towards fidelity of $10^5$–$10^6$. Exonuclease-deficient polymerases, such as (exo$^-$) Klenow or Sequenase 2.0, catalysed incorporation of a nucleotide which was only observed when the complementary dNTP was present, confirming a high fidelity of these enzymes even in the absence of proof-reading exonuclease activity. The main advantage of using (exo$^-$) Klenow DNA polymerase over Sequenase 2.0 is its lower Km for nucleotides, allowing a high rate of nucleotide incorporation even at low nucleotide concentrations. It is also possible to replace all dNTPs with nucleotide analogues or non-natural nucleotides such as dNTPαS, and such analogues may be preferable for use with a DNA polymerase having exonuclease activity.

In certain circumstances, e.g. with longer sample templates, it may be advantageous to use a polymerase which has a lower $k_m$ for incorporation of the correct (matched) nucleotide, than for the incorrect (mismatched) nucleotide. This may improve the accuracy and efficiency of the method. Suitable such polymerase enzymes include the α-polymerase of Drosophila.

In many diagnostic applications, for example genetic testing for carriers of inherited disease, the sample will contain heterozygous material, that is half the DNA will have one nucleotide at the target position and the other half will have another nucleotide. Thus if four aliquots are used in an embodiment according to the invention, two will show a negative signal and two will show half the positive signal. It will be seen therefore that it is desirable to quantitatively determine the amount of signal detected in each sample. Also, it will be appreciated that if two or more of the same base are adjacent the 3'-end of the primer a larger signal will be produced. In the case of a homozygous sample it will be clear that there will be three negative and one positive signal when the sample is in four aliquots.

Further to enhance accuracy of the method, bidirectional sequencing ie. sequencing of both strands of a double-stranded template may be performed. This may be advantageous e.g. in the sequencing of heterozygous material. Conveniently, this may be achieved by immobilising the double-stranded sample template by one strand, e.g. on particles or in a microtitre well, eluting the second strand and subjecting both strands separately to a sequencing reaction by the method of the invention.

In carrying out the method of the invention, any possible contamination of the reagents e.g. the NTP solutions, by PPi is undesirable and may readily be avoided by including a pyrophosphatase, preferably in low amounts, in the reagent solutions. Indeed, it is desirable to avoid contamination of any sort and the use of high purity or carefully purified reagents is preferred, e.g. to avoid contamination by kinases.

Reaction efficiency may be improved by including $Mg^{2+}$ ions in the reagent (NTP and/or polymerase) solutions.

It will be appreciated that when the target base immediately 3'- of the primer has an identical base 3'-thereto, and the polymerisation is effected with a deoxynucleotide (rather than a dideoxynucleotide) the extension reaction will add two bases at the same time and indeed any sequence of successive identical bases in the sample will lead to simultaneous incorporation of corresponding bases into the primer. However, the amount of pyrophosphate liberated will clearly be proportional to the number of incorporated bases so that there is no difficulty in detecting such repetitions.

Since the primer is extended by a single base by the procedure described above (or a sequence of identical bases), the extended primer can serve in exactly the same way in a repeated procedure to determine the next base in the sequence, thus permitting the whole sample to be sequenced.

As mentioned above, in the method of the invention, different deoxy- or dideoxynucleotides may be added to separate aliquots of sample-primer mixture or successively to the same sample-primer mixture. This covers the situations where both individual and multiple target DNA samples are used in a given reaction, which sample DNAs may be the same or different. Thus, for example, as will be discussed in more detail below, in certain embodiments of the invention, there may be one reaction in one container, (in the sense of one sample DNA, ie. one target DNA sequence, being extended) whereas in other embodiments different primer-sample combinations may be present in the same reaction chamber, but kept separate by e.g. area-selective immobilisation.

The present invention provides two principal methods of sequencing immobilised DNA. A. The invention provides a first method of sequencing sample DNA wherein the sample DNA is subjected to amplification; the amplified DNA is optionally immobilised and then subjected to strand separation, one strand eg. the optionally non-immobilised or immobilised strand being removed (ie. either strand may be sequenced), and an extension primer is provided, which primer hybridises to the sample DNA immediately adjacent that portion of the DNA to be sequenced; each of four aliquots of the single stranded DNA is then subjected to a polymerase reaction in the presence of a deoxynucleotide, each aliquot using a different deoxynucleotide whereby only the deoxynucleotide complementary to the base in the target position becomes incorporated; pyrophosphate released by base incorporation being identified. After identification of the incorporated nucleotide a nucleotide degrading enzyme is added. Upon separating the nucleotide degrading enzyme from the different aliquots, for example if it is immobilised on magnetic beads, the four aliquots can be used in a new cycle of nucleotide additions. This procedure can then be continuously repeated. B. The invention also provides a second method of sequencing sample DNA wherein the sample DNA is subjected to amplification; the amplified DNA is optionally immobilised and then subjected to strand separation, one strand eg. the optionally non-immobilised or immobilised strand being removed, and an extension primer is provided, which primer hybridises to the sample DNA immediately adjacent that portion of the DNA to be sequenced; the single stranded DNA is then subjected to a polymerase reaction in the presence of a first deoxynucleotide, and the extent of pyrophosphate release is determined, non-incorporated nucleotides being degraded by the nucleotide-degrading enzyme, and the reaction being repeated by successive addition of a second, third and fourth deoxynucleotide until a positive release of pyrophosphate indicates incorporation of a particular deoxynucleotide into the primer, whereupon the procedure is repeated to extend the primer one base at a time and to determine the base which is immediately 3'- of the extended primer at each stage.

An alternative format for the analysis is to use an array format wherein samples are distributed over a surface, for example a microfabricated chip, and thereby an ordered set of samples may be immobilized in a 2-dimensional format. Many samples can thereby be analysed in parallel. Using the method of the invention, many immobilized templates may be analysed in this way by allowing the solution containing the enzymes and one nucleotide to flow over the surface and then detecting the signal produced for each sample. This procedure can then be repeated. Alternatively, several different oligonucleotides complementary to the template may be distributed over the surface followed by hybridization of the template. Incorporation of deoxynucleotides or dideoxynucleotides may be monitored for each oligonucleotide by the signal produced using the various oligonucleotides as primer. By combining the signals from different areas of the surface, sequence-based analyses may be performed by four cycles of polymerase reactions using the various dideoxynucleotides.

Two-stage PCR (using nested primers), as described in our co-pending application WO90/11369, may be used to enhance the signal to noise ratio and thereby increase the sensitivity of the method according to the invention. By such preliminary amplification, the concentration of target DNA is greatly increased with respect to other DNA which may be present in the sample and a second-stage amplification with at least one primer specific to a different sequence of the target DNA significantly enhances the signal due to the target DNA relative to the 'background noise'.

Regardless of whether one-stage or two stage PCR is performed, the efficiency of the PCR is not critical since the invention relies on the distinct difference different from the aliquots. However, as mentioned above, it is preferred to run an initial qualitative PCR step e.g. by the DIANA method (Detection of Immobilised Amplified Nucleic Acids) as described in WO90/11369 as a check for the presence or absence of amplified DNA.

Any suitable polymerase may be used, although it is preferred to use a thermophilic enzyme such as Taq polymerase to permit the repeated temperature cycling without having to add further polymerase, e.g. Klenow fragment, in each cycle of PCR.

PCR has been discussed above as a preferred method of initially amplifying target DNA although the skilled person will appreciate that other methods may be used instead of in combination with PCR. A recent development in amplification techniques which does not require temperature cycling or use of a thermostable polymerase is Self Sustained Sequence Replication (3SR). 3SR is modelled on retroviral replication and may be used for amplification (see for example Gingeras, T. R. et al PNAS (USA) 87:1874–1878 and Gingeras, T. R. et al PCR Methods and Applications Vol. 1, pp 25–33).

As indicated above, the method can be applied to identifying the release of pyrophosphate when dideoxynucleotide residues are incorporated into the end of a DNA chain. WO93/23562 relates to a method of identification of the base in a single target position in a DNA sequence (minisequencing) wherein sample DNA is subjected to amplification; the amplified DNA is immobilised and then subjected to strand separation, the non-immobilised strand being removed and an extension primer, which hybridises to the immobilised DNA immediately adjacent to the target position, is provided; each of four aliquots of the immobilised single stranded DNA is then subjected to a polymerase reaction in the presence of a dideoxynucleotide, each aliquot using a different dideoxynucleotide whereby only the dideoxynucleotide complementary to the base in the target position becomes incorporated; the four aliquots are then subjected to extension in the presence of all four deoxynucleotides, whereby in each aliquot the DNA which has not reacted with the dideoxynucleotide is extended to form double stranded DNA while the dideoxy-blocked DNA remains as single stranded DNA; followed by identification of the double stranded and/or single stranded DNA to indicate which dideoxynucleotide was incorporated and hence which base was present in the target position. Clearly, the release of pyrophosphate in the chain terminating dideoxynucleotide reaction will indicate which base was incorporated but the relatively large amount of pyrophosphate released in the subsequent deoxynucleotide primer extension reactions (so-called chase reactions) gives a much larger signal and is thus more sensitive.

It will usually be desirable to run a control with no dideoxynucleotides and a 'zero control' containing a mixture of all four dideoxynucleotides.

WO93/23562 defines the term 'dideoxynucleotide' as including 3'-protected 2'-deoxynucleotides which act in the same way by preventing further chain extension. However, if the 3' protecting group is removable, for example by hydrolysis, then chain extension (by a single base) may be followed by unblocking at the 3' position, leaving the extended chain ready for a further extension reaction. In this way, chain extension can proceed one position at a time without the complication which arises with a sequence of identical bases, as discussed above. Thus, the methods A and B referred to above can be modified whereby the base added at each stage is a 3'-protected 2'-deoxynucleotide and after the base has been added (and the light emission detected), the 3'-blocking group is removed to permit a further 3'-protected - 2' deoxynucleotide to be added. Suitable protecting groups include acyl groups such as alkanol groups e.g. acetyl or indeed any hydroxyl protecting groups known in the art, for example as described in Protective Groups in Organic Chemistry, JFW McOnie, Plenum Press, 1973.

The invention, in the above embodiment, provides a simple and rapid method for detection of single base changes. In one format it successfully combines two techniques: solid-phase technology (DNA bound to magnetic beads) and an Enzymic Luminometric Detection Assay (ELIDA). The method can be used to both identify and quantitate selectively amplified DNA fragments. It can also be used for detection of single base substitutions and for estimation of the heterozygosity index for an amplified polymorphic gene fragment. This means that the method can be used to screen for rare point mutations responsible for both acquired and inherited diseases, identify DNA polymorphisms, and even differentiate between drug-resistant and drug-sensitive strains of viruses or bacteria without the need for centrifugations, filtrations, extractions or electrophoresis. The simplicity of the method renders it suitable for many medical (routine analysis in a wide range of inherited disorders) and commercial applications.

The positive experimental results presented below clearly show the method of the invention is applicable to an on-line automatic non-electrophoretic DNA sequencing approach, with step-wise incorporation of single deoxynucleotides. After amplification to yield single-stranded DNA and annealing of the primer, the template/primer-fragment is used in a repeated cycle of dNTP incubations. Samples are continuously monitored in the ELIDA. As the synthesis of DNA is accompanied by release of inorganic pyrophosphate (PPi) in an amount equal to the amount of nucleotide incorporated, signals in the ELIDA are observed only when complementary bases are incorporated. Due to the ability of the method to determine PPi quantitatively, it is possible to distinguish incorporation of a single base from two or several simultaneous incorporations. Since the DNA template is preferably obtained by PCR, it is relatively straight forward to increase the amount of DNA needed for such an assay.

As mentioned above our results open the possibility for a novel approach for large-scale non-electrophoretic DNA sequencing, which allows for continuous determination of the progress of the polymerisation reaction with time. For the success of such an approach there is a need for high efficiency of the DNA polymerase due to the rapid increase of background signal if templates accumulate which are not "in phase". The new approach has several advantages as compared to standard sequencing methods. Firstly, the method is suitable for handling of multiple samples in parallel. Secondly, relatively cost-effective instruments can be envisioned. In addition, the method avoids the use of electrophoresis and thereby the loading of samples and casting of gels.

A further advantage of the method of the present invention is that it may be used to resolve sequences which cause compressions in the gel-electrophoretic step in standard Sanger sequencing protocols.

The method of the invention may also find applicability in other methods of sequencing. For example, a number of iterative sequencing methods, advantageously permitting sequencing of double-stranded targets, based on ligation of probes or adaptors and subsequent cleavage have been described (see e.g. U.S. Pat. No. 5,599,675 and Jones, BioTechniques 22: 938–946, 1997). Such methods generally involve ligating a double stranded probe (or adaptor) containing a Class IIS nuclease recognition site to a double stranded target (sample) DNA and cleaving the probe/adaptor-target complex at a site within the target DNA, one or more nucleotides from the ligation site, leaving a shortened target DNA. The ligation and cleavage cycle is then repeated. Sequence information is obtained by identifying one or more nucleotides at the terminus of the target DNA. The identification of the terminal nucleotide(s) may be achieved by chain extension using the method of the present invention.

Further to permit sequencing of a double stranded DNA, the method of the invention may be used in a sequencing protocol based on strand displacement, e.g. by the introduction of nicks, for example as described by Fu et al., in Nucleic Acids Research 1997, 25(3): 677–679. In such a method the sample DNA may be modified by ligating a double-stranded probe or adaptor sequence which serves to introduce a nick e.g. by containing a non- or mono-phosphorylated or dideoxy nucleotide. Use of a strand-displacing polymerase permits a sequencing reaction to take place by extending the 3' end of probe/adaptor at the nick, nucleotide incorporation being detected according to the method of the present invention.

Advantageously, the method according to the present invention may be combined with the method taught in WO93/23563 which uses PCR to introduce loop structures which provide a permanently attached 3' primer at the 3' terminal of a DNA strand of interest. For example, in such a modified method, the extension primer is introduced as part of the 3'-terminal loop structure onto a target sequence of one strand of double stranded DNA which contains the target position, said target sequence having a region A at the 3'-terminus thereof and there being optionally a DNA region B which extends 3' from region A, whereby said double-stranded DNA is subjected to polymerase chain reaction (PCR) amplification using a first primer hybridising to the 3'-terminus of the sequence complementary to the target sequence, which first primer is immobilised or provided with means for attachment to a solid support, and a second primer having a 3'-terminal sequence which hybridises to at least a portion of A and/or B of the target sequence while having at its 5'-end a sequence substantially identical to A, said amplification producing double-stranded target DNA having at the 3'-end of the target sequence, in the following order, the region A, a region capable of forming a loop and a sequence A' complementary to sequence A, whereafter the amplified double-stranded DNA is subjected in immobilised form to strand separation whereby the non-immobilised target strand is liberated and region A' is permitted or caused to hybridise to region A, thereby forming said loop. The 3' end of region A' hybridises immediately adjacent the target position. The dideoxy and/or extension reactions use the hybridised portion as a primer.

The method of the invention may also be used for real-time detection of known single-base changes. This concept relies on the measurement of the difference in primer extension efficiency by a DNA polymerase of a matched over a mismatched 3' terminal. The rate of the DNA polymerase catalyzed primer extension is measured by the ELIDA as described previously. The PPi formed in the polymerization reaction is converted to ATP by ATP sulfurylase and the ATP production is continuously monitored by the firefly luciferase. In the single-base detection assay, single-stranded DNA fragments are used as template. Two detection primers differing with one base at the 3'-end are designed; one precisely complementary to the non-mutated DNA-sequence and the other precisely complementary to the mutated DNA-sequence. The primers are hybridized with the 3'-termini over the base of interest and the primer extension rates are, after incubation with DNA polymerase and deoxynucleotides, measured with the ELIDA. If the detection primer exactly matches to the template a high extension rate will be observed. In contrast, if the 3'-end of the detection primer does not exactly match to the template (mismatch) the primer extension rate will be much lower. The difference in primer extension efficiency by the DNA polymerase of a matched over a mismatched 3'-terminal can then be used for single-base discrimination. Thus, the presence of the mutated DNA sequence can be distinguished over the non-mutated sequence. The relative mismatch extension efficiencies may be strongly decreased by substituting the α-thiotriphosphate analog for the next correct natural deoxynucleotide after the 3'-mismatch termini. By performing the assay in the presence of a nucleotide degrading enzyme. It is easier to distinguish between a match and a mismatch of the type that are easy to extend, such as A:T, T:G and C:T.

The invention also comprises kits for use in methods of the invention which will normally include at least the following components:

(a) a test specific primer which hybridises to sample DNA so that the target position is directly adjacent to the 3' end of the primer;
(b) a polymerase;
(c) detection enzyme means for identifying pyrophosphate release;
(d) a nucleotide-degrading enzyme;
(e) deoxynucleotides, or optionally deoxynucleotide analogues, optionally including, in place of dATP, a dATP analogue which is capable of acting as a substrate for a polymerase but incapable of acting as a substrate for a said PPi-detection enzyme; and
(f) optionally dideoxynucleotides, or optionally dideoxynucleotide analogues, optionally ddATP being replaced by a ddATP analogue which is capable of acting as a substrate for a polymerase but incapable of acting as a substrate for a said PPi-detection enzyme.

If the kit is for use with initial PCR amplification then it will also normally include at least the following components:

(i) a pair of primers for PCR, at least one primer having means permitting immobilisation of said primer;
(ii) a polymerase which is preferably heat stable, for example Taq1 polymerase;
(iii) buffers for the PCR reaction; and
(iv) deoxynucleotides.

The invention will now be described by way of a non-limiting Example with reference to the drawings.

EXAMPLE 1

MATERIALS AND METHODS

Synthesis and purification of oligonucleotides

The oligonucleotides PEBE25 SEQ ID NO:1 (35-mer: 5'-GCAACGTCGCCACACACAACATACGAGCCGGA AGG-3'), RIT 27 SEQ ID NO:2 (23-mer: 5'-GCTTCCGGCTCGTATGTTGTGTG-3'), E3PN SEQ ID NO:3 (35-mer: 5'-GCTGGAATTCGTCAGACTGG CCGTCGTTTTACAAC-3'), NUSPT SEQ ID NO:4 (17-mer: 5'-GTAAAACGACGGCCA-GT-3'), RIT 203 SEQ ID NO:5 (51-mer: 5'-AGCTTGGGTTCGAGGAGATCTTCC GGGTTACGGCGGAAGATCTCCTCGAGG-3), RIT 204 SEQ ID NO:6 (51-mer: 5'-AGCTCC-TCGAGGAGATCT TCCGCCGTAACCCGGAAGATCTCCTCGAACCCA-3'), ROMO 205S SEQ ID NO:7 5'-CGAGGAGATCTTCCG GGTTACGGCG-3'), ROMO 205B SEQ ID NO:8 (25-mer: 5'-biotin-CGAGGAGATCTTCCGGGTTACGGCG-3') RIT 28, RIT 29, and USP (Hultman et al., 1990, Nucleic Acids Research, 18, 5107–5112) were synthesised by phosphoramidite chemistry on an automated DNA synthesis apparatus (Gene Assembler Plus, Pharmacia Biotech, Uppsala, Sweden). Purification was performed on a fast protein liquid chromatography pepRPC 5/5 column (Pharmacia Biotech).

In Vitro Amplification and Template Preparation

PCR reactions were performed on the multilinker of plasmid pRT 28 with 7.5 pmol of general primers, RIT 28 and RIT 29 (biotinylated), according to Hultman et al. (supra). The biotinylated PCR products were immobilised onto streptavidin-coated super paramagnetic beads Dynabead™ M280-Streptavidin, or M450-Streptavidin (Dynal, A. S., Oslo, Norway). Single-stranded DNA was obtained by removing the supernatant after incubation of the immobilised PCR product in 0.10 M NaOH for 5 minutes. Washing of the immobilised single-stranded DNA and hybridization to sequencing primers was carried out as described earlier (Nyren et al., 1993, Anal. Biochem. 208, 171–175).

Construction of the Hairpin Vector DRIT 28HP and Preparation of PCR Amplified Template The oligonucleotides RIT 203, and RIT 204 were hybridized and ligated to HindII (Pharmacia Biotech) pre-restricted plasmid PRIT 28 (the obtained plasmid was named pRIT 28HP). PCR reaction was performed on the multilinker of plasmid pRIT 28HP with 7.5 pmol of primer pairs, RIT 29/ROMO 205S or RIT 27/ROMO 205B, 200 µM DNTP, 20 mM Tris-HCl (pH 8.7), 2 mM $MgCl_2$, 0.1% Tween 20, and 1 unit AmplitTaq DNA polymerase making up a final volume of 50 µl. The temperature profile included a 15 second denaturation step at 95° C. and a 90 second hybridization/extension step at 72° C. These steps were repeated 35 times with a GeneAmp PCR System, 9600 (Perkin, Elmer, Emeryville, USA). The immobilised (as described above) single-stranded DNA obtained from the RIT 29/ROMO 205S amplified reaction or the non-biotinylated single-stranded DNA fragment from the RIT 27/ROMO 205B amplified reaction, was allowed to hybridize at 65° C. for 5 minutes in 20 mM Tris-HCl (pH 7.5), 8 mM $MgCl_2$ to make a self-priming loop structure.

DNA Sequencing

The oligonucleotides E3PN, PEBE25, and the above described PCR products were used as templates for DNA sequencing. The oligonucleotides E3PN, PEBE25, and single-stranded RIT 28/RIT 29 amplified PCR product were hybridized to the primers NUSPT, RIT 27, and NUSPT, respectively. The hybridized DNA-fragments, or the self-primed loop-structures were incubated with either a modified T7 DNA polymerase (Sequenase 2.0; U.S. Biochemical, Cleveland, Ohio, USA), or exonuclease deficient (exo⁻) Klenow DNA polymerase (Amersham, UK). The sequencing procedure was carried out by stepwise elongation of the primer strand upon sequential addition of the different deoxynucleoside triphosphates (Pharmacia Biotech), and simultaneous degradation of nucleotides by apyrase. The PPi released due to nucleotide incorporation was detected by the ELIDA. The produced ATP and the non-incorporated deoxynucleotide were degraded in real-time by apyrase. The luminescence was measured using an LKB 1250 luminometer connected to a potentiometric recorder. The luminometer was calibrated to give a response of 10 mV for the internal light standard. The luminescence output was calibrated by the addition of a known amount of ATP or PPi. The standard assay volume was 0.2 ml and contained the following components: 0.1 M Tris-acetate (pH 7.75), 2 mM EDTA, 10 mM magnesium acetate, 0.1% bovine serum albumin, 1 mM dithiothreitol, 2 µM adenosine 5'-phosphosulfate (APS), 0.4 mg/ml polyvinylpyrrolidone (360 000), 100 µg/ml D-100 µg/ml D-luciferin (Bio Therma, Dalarö, Sweden), 4 µg/ml L-luciferin (Bio Therma, Dalarö, Sweden), 120–240 mU/ml ATP sulfurylase (ATP:sulfate adenylyl transferase; EC 2.7.7.4) (Sigma Chemical Co.), 100–400 mU apyrase (nucleoside 5'-triphosphatase and nucleoside 5'-diphosphatase; EC 3.6.1.5) (Sigma Chemical Co.), purified luciferase (Sigma Chemical Co.) in an amount giving a response of 200 mV for 0.1 µM ATP. One to five pmol of the DNA-fragment, and 3 to 15 pmol DNA polymerase were added to the solution described above. The sequencing reaction was started by adding 0.2–1.0 nmol of one of the deoxynucleotides (Pharmacia Biotech). The reaction was carried out at room temperature.

Conventional DNA Sequencing

The sequencing data obtained from the new DNA sequencing were confirmed by semiautomated solid-phase sequencing using radioactive labelled terminators (Hultman et al., 1991, BioTechniques, 10, 84–93). The produced Sanger fragment, from the loop-structured PCR product were restricted by Bgl II restriction endonuclease prior to gel loading.

RESULTS

Principle of the DNA Sequencing Method

The principle of the new sequencing method is illustrated in FIG. 1. A specific DNA-fragment of interest (sequencing primer hybridized to a single-stranded DNA template, or self-primed single-stranded product) is incubated with DNA polymerase, ATP sulfurylase, luciferase and a nucleotide degrading enzyme, and a repeated cycle of nucleotide incubation is performed. The synthesis of DNA is accompanied by release of PPi equal in molarity to that of the incorporated nucleotide. Thereby, real-time signals are obtained by the enzymatic inorganic pyrophosphate detection assay (ELIDA) only when complementary bases are incorporated. In the ELIDA the produced PPi is converted to ATP by ATP sulfurylase and the amount of ATP is then determined by the luciferase assay (FIG. 1). As added nucleoticles are continuously degraded by a nucleotide degrading enzyme a new nucleotide can be added after a specific time-interval. From the ELIDA results the sequence after the primer is deduced. The DNA sequencing method of the invention is named "pyrosequencing".

Optimization of the Method

Several different parameters of the new DNA sequencing approach were optimised in a model system using a synthetic DNA template. As the method is based on utilization, of added deoxynucleotides by the DNA polymerase detection of released PPi by a coupled enzymatic system and continuous degradation of nucleotides, the concentration of the different components used in the assay should be carefully balanced.

Figure 2:
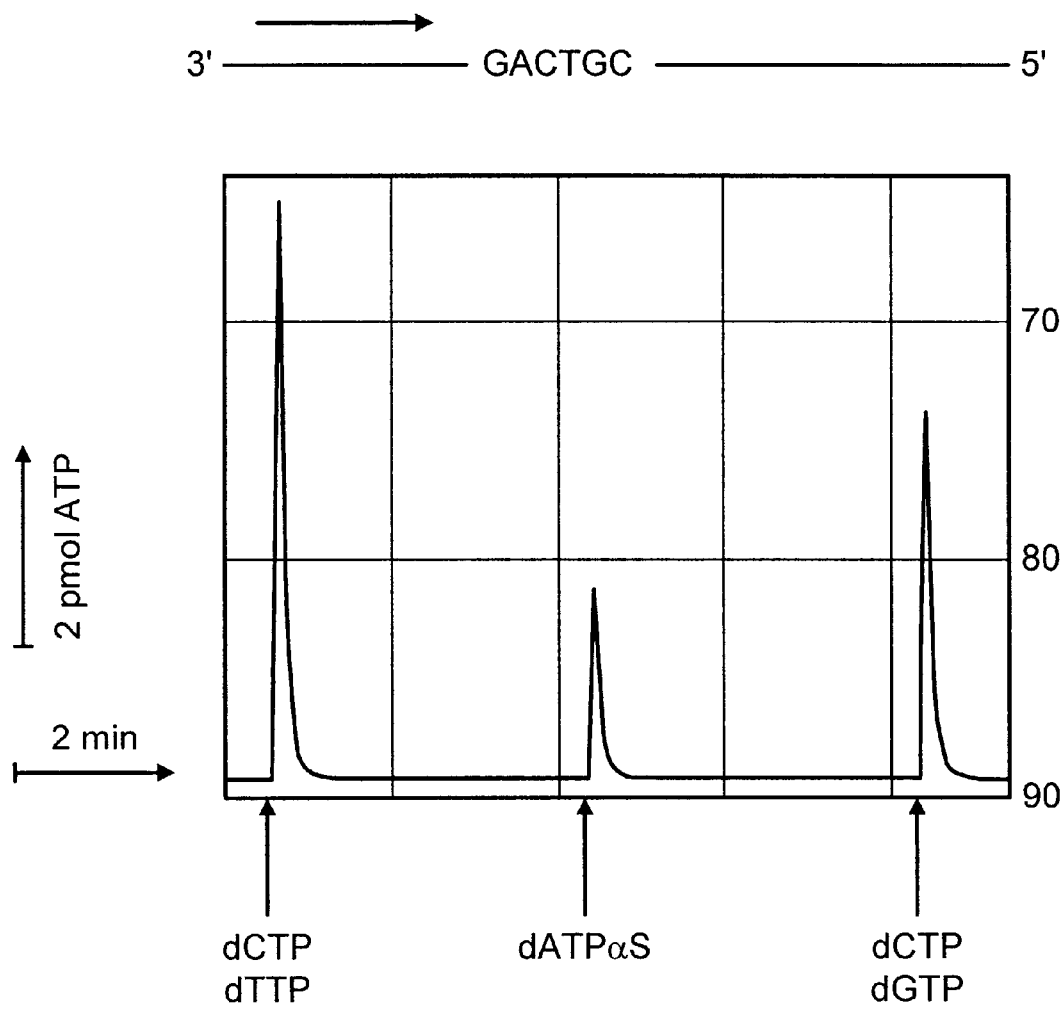
FIG. 2 shows DNA sequencing on a 35-base long oligonucleotide template. About 2 pmol of the template/primer (E3PN/NUSPT) were incubated with 4 pmol (exo$^-$) Klenow and 0.2 U apyrase. The reaction was started by the addition of 0.4 nmol of each of the indicated deoxynucleotides and the PPi released was detected in real-time by the ELIDA. The DNA-sequence of the template is shown in the Figure. The experimental conditions are as described in Example 1.

The signal-extent as a function of the numbers of correct deoxynucleotides added is shown in FIG. 2. The reaction was started by addition of the three first correct bases (dCTP, dTTP and dGTP) and the trace show both the release of PPi (converted to ATP by the ATP sulfurylase) during the incorporation of the bases, and the subsequent degradation of ATP. The incorporation of three residues was noted. After a short time-lag (the apyrase reaction was allowed to proceed about 2 minutes), dATPuS was added; a signal corresponding to incorporation of one residue was observed. Thereafter, the two next correct deoxynucleotides (dCTP and dGTP) were added. This time the incorporation of two residues was detected. The results illustrated in FIG. 2 show that the DNA sequencing approach functions; the added deoxynucleotides were degraded by apyrase between each addition, the observed signals were proportional to the amount of nucleotide incorporated, and no release of PPi was observed if a non-complementary base was added (not shown).

In the above illustrated experiment, 32 mU ATP sulfurylase, 200 mU apyrase, 2 U (exo⁻) Klenow, 2 pmol template/primer, and 0.4 pmol deoxynucleotides, were used. Similar results were obtained (not shown) when the different compounds were varied within the interval: 24–48 mU ATP sulfurylase, 100–400 mU apyrase, 1–5 U (exo⁻) Klenow, 1–5 pmol template/primer, and 0.2–1.0 nmol deoxynucleotides. It may be important to use an excess of polymerase over primer/template to be sure that all free 3' ends are extended. It may also be important that the sequencing primer hybridize at least one base inside from the 3' end of the template to eliminate blunt-end DNA polymerase activity (Clark, 1991, Gene, 104, 75–80).

DNA Sequencing

Figure 3:
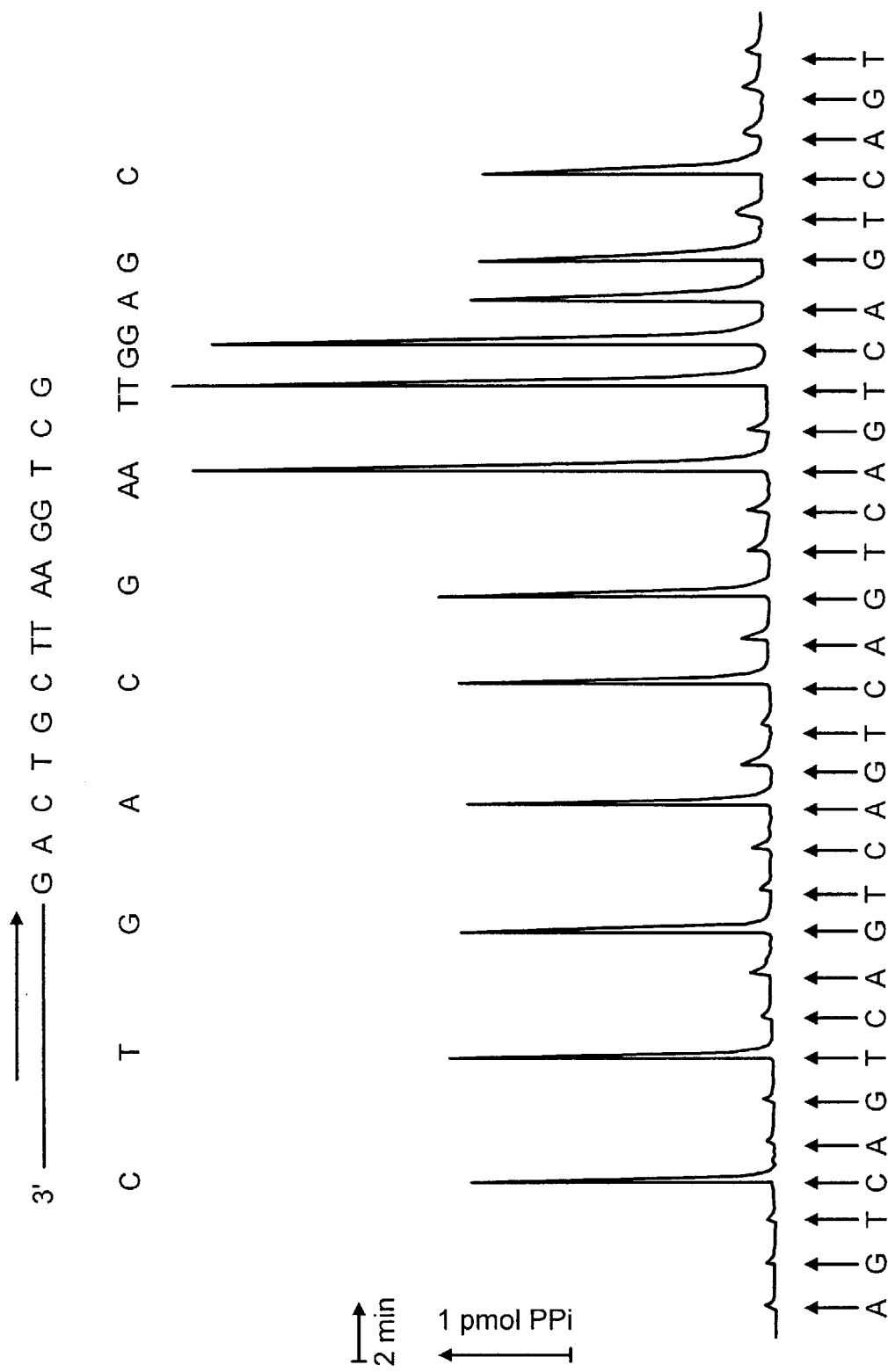
FIG. 3 shows DNA sequencing on a 35-base-long oligonucleotide template. About 5 pmol of the template/primer (E3PN/NUSPT) were incubated with 8 pmol (exo$^-$) Klenow and 0.2 U apyrase. The reaction was started by the addition of 0.4 nmol of the indicated deoxynucleotide and the PPi released was detected by the ELIDA. The DNA-sequence of the template is shown in the Figure. The experimental conditions were as described in Example 1.
Figure 4:
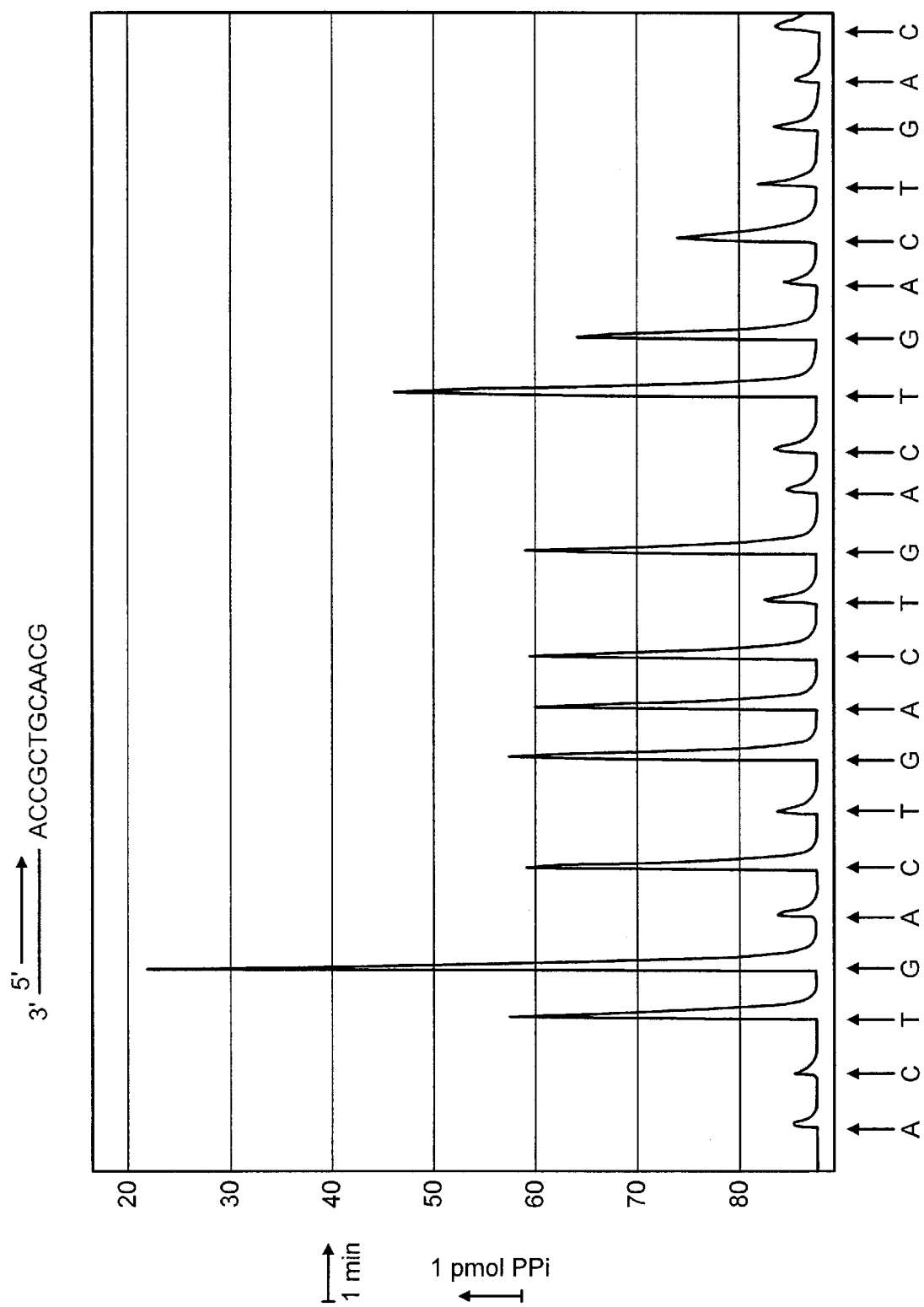
FIG. 4 shows DNA sequencing on a 35-base-long oligonucleotide template. About 5 pmol of the template/primer (PEBE25/RIT27) were incubated with 8 pmol (exo⁻) Klenow and 0.2 U apyrase. The reaction was started by the addition of 0.4 nmol of the indicated deoxynucleotide and the PPi released was detected by the ELIDA. The DNA-sequence of the template is shown in the Figure. The experimental conditions were as described in Example 1.
Figure 5:
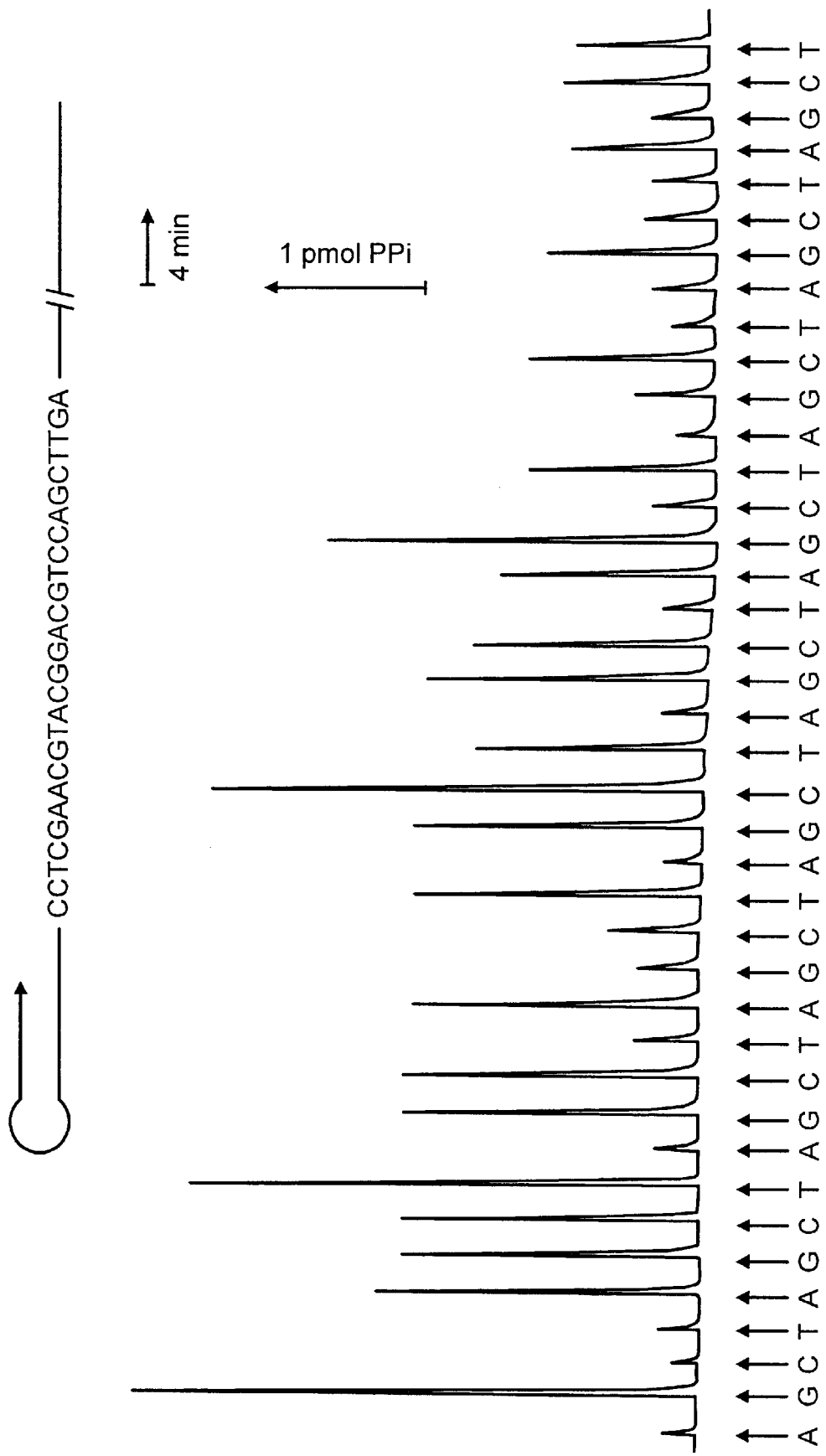
FIG. 5 shows real-time DNA sequencing performed on a 160-base-long single-stranded PCR product. About 5 pmol of the template/primer (NUSPT) were incubated with 8 pmol (exo⁻) Klenow and 0.2 U apyrase. The reaction was started by the addition of 0.4 nmol of the indicated deoxynucleotide and the PPi released was detected by the ELIDA. The DNA-sequence after the primer is shown in the Figure. The experimental conditions were as described in Example 1.

In the next series of experiments two different synthetic templates as well as a PCR product were sequenced in order to investigate the feasibility of the new approach. FIGS. 3 and 4 show the result from DNA sequencing performed on two different synthetic templates. Both templates were sequenced to the end, and in both cases the true sequence could be determined. When the polymerase reaches the end of the template, the signal strongly decreases indicating slower polymerization for the last bases. The signal was not decreased to the same extent if a longer template was sequenced (FIG. 5). The small signals observed when non-complementary bases were added are due to PPi contamination in the nucleotide solutions. The later increase of this background signal (false signals) is probably due to nucleoside diphosphate kinase activity (contamination in the ATP sulfurylase preparation from Sigma). The nucleoside diphosphate kinase converts non-degraded deoxynucleoside diphosphates to deoxynucleoside triphosphates when a new deoxynucleotide triphosphate is added. The formed deoxynucleoside triphosphate can then be incorporated into the growing primer. This effect was especially obvious when the synthetic template E3PN as sequenced. When the first correct nucleotide (dCTP) is added some of the non-degraded dTDP is converted to dTTP. After dCMP has been incorporated some of the formed dTTP can be incorporated. This out-of-phase obtained DNA can be further extended when dGTP is added. This is clearly shown when the out-of-phase DNA has reached the position where two A should be incorporated. The false signal is now stronger. The following double T and C also give stronger signals whereas the next single A gives a lower signal. In FIG. 5, DNA sequencing of 20 bases of a 160-base-long self-primed single-stranded PCR product is shown. The obtained sequence was confirmed by semiautomatic solid-phase Sanger sequencing (data not shown). The main reason for the sequencing to come out of phase is a combination of slow degration of deoxynucleoside diphosphates (at least some of the dNDPs) by the potato apyrase (Liebecq, C. Lallemand A, and Deguldre-Guillaume, M. J. (1963) Bull. Soc. Chim. Biol. 45, 573–594) and the deoxynucleoside diphosphate kinase contamination in the ATP sulfurylase preparation obtained from Sigma. It is possible to overcome this problem by using a pure preparation of ATP sulfurylase, or by using more efficient dNDP degrading enzymes (Doremus, H. D. and Blevins, D. G. (1988) Plant Physiol. 87(1), 41–45). Even if a pure preparation of ATP sulfurylase is used it could be an advantage to use combinations of nucleotide degrading enzymes (NTPase, NDPase, NMPase) to increase the rate of the degradation process and to decrease the thermodynamic equilibrium concentration of dNTPs. In addition, it could be an advantage to use an enzyme with low Km for dNTPs such as the Pig Pancreas nucleoside triphosphate diphosphohydrolase (Le Bel, D., Piriet, G. G. Phaneuf, S., St-Jean, P., Laliberte, J. F. and Beudoin, A. R. (1980) J. Biol. Chem. 255, 1227–1233; Laliberte, J. F. St-Jean, P. and Beudoin, R. (1982) J. Biol Chem. 257, 3869–3871).

EXAMPLE 2

PyroSequencing" on a PCR Product

Figure 6:
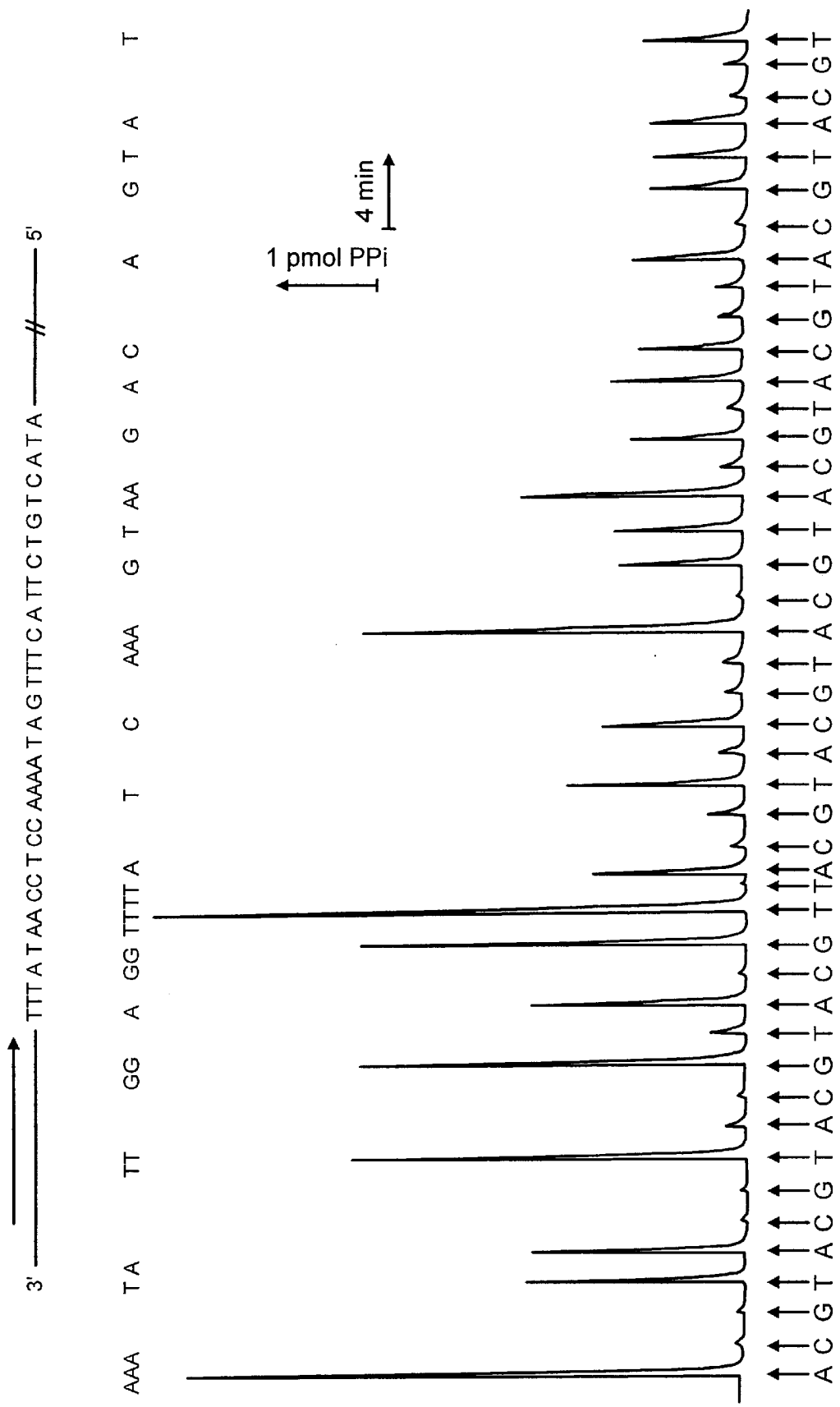
FIG. 6 shows the sequencing method of the invention performed on a 130-base-long single-stranded PCR product hybridized to the sequencing primer as described in Example 2. About 2 pmol of the template/primer was used in the assay. The reaction was started by the addition of 0.6 nmol of the indicated deoxynucleotide and the PPi released was detected by the described method. The DNA-sequence after the primer is indicated in the Figure.

The biotinylated PCR products were immobilized onto streptavidin-coated super paramagnetic beads Dynabeads™ M280-Streptavidin (Dynal). Elution of single-stranded DNA and hybridization of sequencing primer (JA 80 5'-GATGGAAACCAAAAATGATAGG-3') SEQ ID NO:9 was carried out as described earlier (T. Hultman, M. Murby, S. Ståhl, E. Hornes, M. Uhlén, Nucleic Acids Res. 18: 5107 (1990)). The hybridized template/primer were incubated with Sequenase 2.0 DNA polymerase (Amersham). The sequencing procedure was carried out by stepwise elongation of the primer-strand upon sequential addition of the different deoxynucleoside triphosphates (Pharmacia Biotech), and simultaneous degradation of nucleotides by apyrase. The apyrase was grade VI, high ATPase/ADPase ratio (nucleoside 51-triphosphatase and nucleoside 5'-diphosphatase; EC 3.61.5) (Sigma Chemical Co.). The sequencing reaction was performed at room temperature and started by adding 0.6 nmol of one of the deoxynucleotides (Pharmacia Biotech). The PPi released due to nucleotide incorporation was detected as described earlier (see e.g. Example 1). The JA80 was synthesized by phosphoramidite chemistry (Interactiva). The sequencing data obtained from the PyroSequencing method was confirmed by semi-automated solid-phase Sanger sequencing according to Hultman et al. (T. Hultman, M. Murby, S. Ståhl, E. Hornes, M. Uhlén, Nucleic Acids Res. 18: 5107 (1990)). The reaction was carried out at room temperature. The results are shown in FIG. 6.

What is claimed is:

1. A method of identifying a base at a target position in a sample DNA sequence comprising providing a sample DNA sequence and an extension primer, which hybridizes to the sample DNA immediately adjacent to the target position and subjecting the sample DNA and extension primer to a polymerase reaction in the presence of a deoxynucleotide or dideoxynucleotide whereby the deoxynucleotide or dideoxynucleotide will only become incorporated and release pyrophosphate (PPi) if it is complementary to the base in the target position, and detecting any release of PPi enzymically, different deoxynucleotides or dideoxynucleotides being added either to separate aliquots of sample-primer mixture or successively to the sample-primer mixture and subjected to the polymerase reaction to indicate which deoxynucleotide or dideoxynucleotide is incorporated, wherein a nucleotide-degrading enzyme is included during the polymerase reaction step, such that unincorporated nucleotides are degraded, and whereby any release of PPi is indicative of incorporation of deoxynucleotide or dideoxynucleotide and the identification of a base complementary thereto.

2. A method as claimed in claim 1, wherein the nucleotide-degrading enzyme is apyrase.

3. A method as claimed in claim 1, wherein a mixture of nucleotide-degrading enzymes is used having nucleoside triphosphatase, nucleoside diphosphatase and nucleoside monophosphatase activity.

4. A method as claimed in claim 1, wherein the nucleotide-degrading enzyme is immobilised on a solid support.

5. A method as claimed in claim 4, wherein said immobilised nucleotide-degrading enzyme is added after nucleotide incorporation by the polymerase has taken place, and then removed prior to a subsequent nucleotide incorporation reaction step.

6. A method as claimed in claim 1, wherein PPi release is detected using the Enzymatic Luminometric Inorganic Pyrophosphate Detection Assay (ELIDA).

7. A method as claimed in claim 1, wherein the PPi detection enzymes are included in the polymerase reaction step and the polymerase reaction and PPi release detection steps are performed substantially simultaneously.

8. A method as claimed in claim 1, wherein in the polymerase reaction a dATP or ddATP analogue is used which is capable of acting as a substrate for a polymerase but incapable of acting as a substrate for a PPi detection enzyme.

9. A method as claimed in claim 8, wherein the dATP analogue is deoxyadenosine α-thiotriphosphate (dATPαS).

10. A method as claimed in claim 1, further comprising the use of the α-thio analogues of dCTP, dGTP and dTTP.

11. A method as claimed in claim 1, wherein the sample DNA is immobilised or provided with means for attachment to a solid support.

12. A method as claimed in claim 1, wherein the sample DNA is first amplified.

13. A method as claimed in claim 1, wherein the extension primer contains a loop and anneals back on itself and the 3' end of the sample DNA.

14. A method as claimed in claim 1, wherein an exonuclease deficient (exo⁻) high fidelity polymerase is used.

15. A method as claimed in claim 1, for identification of a base in a single target position in a DNA sequence comprising subjecting the sample DNA to amplification; immobilizing the amplified DNA and then subjecting the immobilized DNA to strand separation, removing the non-immobilized strand and providing an extension primer, which hybridizes to the immobilized DNA immediately adjacent to the target position; subjecting each of four aliquots of the immobilized single stranded DNA to a polymerase reaction in the presence of a dideoxynucleotide, each aliquot using a different dideoxynucleotide whereby only the dideoxynucleotide complementary to the base in the target position becomes incorporated; subjecting the four aliquots to extension in the presence of all four deoxynucleotides, whereby in each aliquot the DNA which has not reacted with the dideoxynucleotide is extended to form double stranded DNA while the dideoxy-blocked DNA remains as single stranded DNA; followed by identifying the double stranded and/or single stranded DNA to indicate which dideoxynucleotide was incorporated and hence which base was present in the target position.

16. A kit for use in a method as defined in claim 1, comprising:
(a) a polymerase;
(b) detection enzyme means for identifying pyrophosphate release;

(c) a mixture of nucleotide-degrading enzymes;
(d) deoxynucleotides, or optionally deoxynucleotide analogues, optionally including, in place of dATP, a dATP analogue which is capable of acting as a substrate for a polymerase but incapable of acting as a substrate for a said PPi-detection enzyme; and
(e) optionally a test specific primer which hybridises to sample DNA so that the target position is directly adjacent to the 3' end of the primer; and
(f) optionally dideoxynucleotides, or optionally dideoxynucleotide analogues, optionally ddATP being replaced by a ddATP analogue which is capable of acting as a substrate for a polymerase but incapable of acting as a substrate for a said PPi-detection enzyme.

17. A method of identifying a base at a target position in a sample DNA sequence comprising arranging a multiplicity of DNA sequences in array format on a solid surface, providing to each sample an extension primer, which hybridizes to the sample DNA immediately adjacent to the target position and subjecting the sample DNA and extension primer to a polymerase reaction in the presence of a deoxynucleotide or dideoxynucleotide whereby the deoxynucleotide or dideoxynucleotide will only become incorporated and release pyrophosphate (PPi) if it is complementary to the base in the target position and detecting any release of PPi enzymically, different deoxynucleotides or dideoxynucleotides being added either to separate aliquots of sample-primer mixture or successively to the same sample-primer mixture and subjected to the polymerase reaction to indicate which deoxynucleotide or dideoxynucleotide is incorporated whereby a nucleotide-degrading enzyme is included during the polymerase reaction step such that unincorporated nucleotides are degraded, and whereby any release of PPi is indicative of incorporation of deoxynucleotide or dideoxynucleotide and the identification of a base complementary thereto.

* * * * *

SEQUENCE LISTING

```
<160> NUMBER OF SEQ ID NOS: 9

<210> SEQ ID NO 1
<211> LENGTH: 35
<212> TYPE: DNA
<213> ORGANISM: Artificial Sequence
<220> FEATURE:
<223> OTHER INFORMATION: Oligonucleotide (PEBE25)
```

<400> SEQUENCE: 1
gcaacgtcgc cacacacaac atacgagccg gaagg                     35

<210> SEQ ID NO 2
<211> LENGTH: 23
<212> TYPE: DNA
<213> ORGANISM: Artificial Sequence
<220> FEATURE:
<223> OTHER INFORMATION: Oligonucleotide (RIT 27)

<400> SEQUENCE: 2
gcttccggct cgtatgttgt gtg                                  23

<210> SEQ ID NO 3
<211> LENGTH: 35
<212> TYPE: DNA
<213> ORGANISM: Artificial Sequence
<220> FEATURE:
<223> OTHER INFORMATION: Oligonucleotide (E3PN)

<400> SEQUENCE: 3
gctggaattc gtcagactgg ccgtcgtttt acaac                     35

<210> SEQ ID NO 4
<211> LENGTH: 17
<212> TYPE: DNA
<213> ORGANISM: Artificial Sequence
<220> FEATURE:
<223> OTHER INFORMATION: Oligonucleotide (NUSPT)

<400> SEQUENCE: 4
gtaaaacgac ggccagt                                         17

<210> SEQ ID NO 5
<211> LENGTH: 51
<212> TYPE: DNA
<213> ORGANISM: Artificial Sequence
<220> FEATURE:
<223> OTHER INFORMATION: Oligonucleotide (RIT 203)

<400> SEQUENCE: 5
agcttgggtt cgaggagatc ttccgggtta cggcggaaga tctcctcgag g   51

<210> SEQ ID NO 6
<211> LENGTH: 51
<212> TYPE: DNA
<213> ORGANISM: Artificial Sequence
<220> FEATURE:
<223> OTHER INFORMATION: Oligonucleotide (RIT 204)

<400> SEQUENCE: 6
agctcctcga ggagatcttc cgccgtaacc cggaagatct cctcgaaccc a   51

<210> SEQ ID NO 7
<211> LENGTH: 25
<212> TYPE: DNA
<213> ORGANISM: Artificial Sequence
<220> FEATURE:
<223> OTHER INFORMATION: Oligonucleotide (ROMO 205S)

<400> SEQUENCE: 7
cgaggagatc ttccgggtta cggcg                                25

<210> SEQ ID NO 8

-continued

```
<211> LENGTH: 25
<212> TYPE: DNA
<213> ORGANISM: Artificial Sequence
<220> FEATURE:
<223> OTHER INFORMATION: Oligonucleotide (ROMO 205B)
<221> NAME/KEY: modified_base
<222> LOCATION: (1)...(1)
<223> OTHER INFORMATION: biotin

<400> SEQUENCE: 8
cgaggagatc ttccgggtta cggcg                                              25

<210> SEQ ID NO 9
<211> LENGTH: 22
<212> TYPE: DNA
<213> ORGANISM: Artificial Sequence
<220> FEATURE:
<223> OTHER INFORMATION: Oligonucleotide (JA 80)

<400> SEQUENCE: 9
gatggaaacc aaaaatgata gg                                                 22
```